NEW AND DISTINCT VARIETY OF GLADIOLUS
Filed Dec. 30, 1970
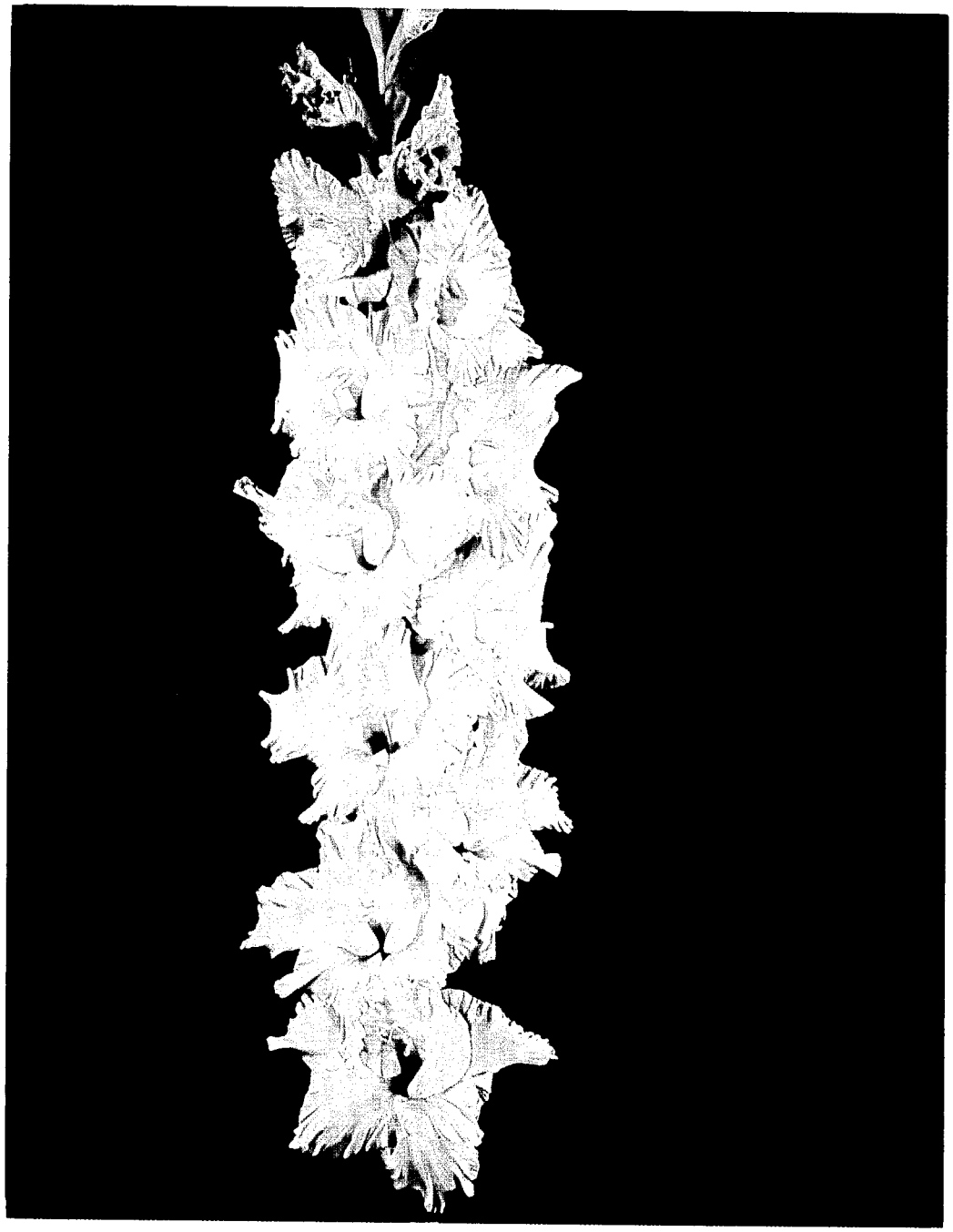

United States Patent Office

Plant Pat. 3,253

Patented Aug. 8, 1972

3,253

NEW AND DISTINCT VARIETY OF GLADIOLUS

John R. Larus, West Hartford, and Charles T. Larus, Avon, Conn., assignors to Selected Glads, Inc., New Albany, Ind.

Filed Dec. 30, 1970, Ser. No. 103,014
Int. Cl. A01h *5/00*
U.S. Cl. Plt.—85 1 Claim

This invention relates to a new and distinct variety of gladiolus plant.

This new gladiolus plant was originated by us by crossing the variety known as "Party Ruffles" (unpatented) with the variety known as "Landmark" (patented as 1,933), "Party Ruffles" being the seed parent, "Landmark" being the pollen parent, both being registered with the North American Gladiolus Registry, published in Sardina, N.Y.

The improved variety resulting from this breeding is evidenced by the following unique combination of characteristics which are outstanding therein and which distinguish our new variety from its parents, as well as from other varieties of which we are aware:

First: Beautiful blend of salmon and orange colors in flowers.

Second: The ability to open one-half of its florets before the first one fades.

In addition to these major characteristics our variety is also endowed with the following characteristics:

(1) Unusually consistent and vigorous foliage and spike growth;
(2) Beauty of form and floret;
(3) Exceptionally tall with long flowerhead;
(4) Good health;
(5) Excellent propagative powers; and
(6) Heavy ruffling.

We have asexually reproduced the new variety by cormels through several generations in Connecticut, and succeeding generations have established that the distinguishing characteristics of the variety held true through propagations by plantings derived from cormels.

The accompanying drawing shows a typical specimen of a flower spike of the new variety, with the flowers in varied stages of growth. Some are shown as partially opened buds and others as fully opened buds. The colors depicted are as nearly true as is possible to achieve photographically.

The following is a detailed description of our new variety, with color terminology in accordance with the Horticultural Colour Charts issued by the British Colour Council and the Royal Horticultural Society, except where general color terms of ordinary dictionary significance are obvious.

*Plant*

Growth: Vigorous and strong; good propagator.

Blooming habit: Under normal conditions the first bloom appears approximately 95 days, in northern latitudes of the United States, after planting.

Stems:

*Form.*—Husky and tall.

*Diameter at base.*—About ¾ to 1 inch.

*Color at base.*—Greenish white—stem and sheaths above the base are light green.

Foliage: Above the ground foliage is rich green, husky and tall. The average leaf is 1½ to 2 inches wide at the base, grows 48 inches long, and tapers.

Disease resistance: The variety has been found to be unusually resistant to the usual gladiolus plant diseases of a bacterial, viral or fungoid genesis.

Corms: Round and high crowned with wrinkled skin. Husk has a tan-white cast.

*Color of flesh.*—Naples yellow—Plate 403/3.

*Flower*

Spike:

*Form and size.*—Exceptionally tall, with bloom spike 72 inches in height and regularly carrying 20 to 24 buds with flowerhead ranging about 30 to 34 inches long.

Bud:

*Size.*—About 3½ inches long when opening.

*Opening.*—Eight to thirteen open at one time with nine showing color at a time.

Flower:

*Arrangement.*—Flowerhead of the new variety has a formal placement wherein all florets face forward.

*Size.*—Individual florets average 4½ to 5 inches in diameter.

*Form.*—Heavily ruffled with petals knuckled in area of throat. Substance is heavy.

*Keeping qualities.*—The flowers are long lasting.

Petals:

*Shape.*—Oval with somewhat needlepoint tips.

*Size.*—Upper petals—about 2 inches wide. Lip petals—about 2 inches wide.

*Aspect.*—Substance is average. Surface is uneven and ruffled.

*Fragrance.*—None.

*Color.*—Shades of Spanish orange ranging from Plate 010/3 to 010. Deepest color is in throat.

*Reproductive organs*

Stamens:

*Color.*—Cream—Plate 433/3.

Pistils:

*Color.*—Cream—Plate 433/3.

*Growth*

Locality where grown and observed: West Hartford, Conn.

Propagation: Holds its distinguishing characteristics through succeeding propagations from cormels.

This variety resembles "Landmark," but it is taller of spike and foliage. Florets are salmon orange instead of cream and somewhat smaller than those of "Landmark."

What we claim is:

1. A new and distinct variety of gladiolus plant, substantially as herein shown and described, characterized particularly as to novelty by the unique combination of its salmon, orange color, and the ability to open one-half of its florets before the first one fades.

No references cited.

ROBERT E. BAGWILL, Primary Examiner